United States Patent [19]

Doyle

[11] Patent Number: 4,657,390
[45] Date of Patent: Apr. 14, 1987

[54] UNIVERSAL SPECTROMETER SYSTEM HAVING MODULAR SAMPLING CHAMBER

[75] Inventor: Walter M. Doyle, Laguna Beach, Calif.

[73] Assignee: Laser Precision Corporation, Utica, N.Y.

[21] Appl. No.: 703,762

[22] Filed: Feb. 21, 1985

[51] Int. Cl.$^4$ .......................... G01B 9/02; G01J 3/45; G01N 21/13

[52] U.S. Cl. .................................... 356/346; 356/244

[58] Field of Search ............... 356/346, 244, 342, 432, 356/319, 326

[56] References Cited

U.S. PATENT DOCUMENTS

| | | | |
|---|---|---|---|
| 3,806,259 | 4/1974 | Boostrom et al. | 356/244 |
| 4,120,592 | 10/1978 | Fleming et al. | 356/432 |
| 4,286,877 | 9/1981 | Clarke | 356/346 |

FOREIGN PATENT DOCUMENTS 2110836  6/1983  United Kingdom ............... 356/319

OTHER PUBLICATIONS

"Beckman Beam Condenser for IR-4200" Beckman Instructions 015-555357, Oct. 1976, pp. 1–4.

*Primary Examiner*—Vincent P. McGraw
*Attorney, Agent, or Firm*—Thomas J. Plante

[57] ABSTRACT

A spectrometer system is disclosed in which the sample-containing chamber is a separately constructed, enclosed modular unit which is readily attachable to, and detachable from, one wall of a housing which constitutes the basic unit of the spectrometer, and which contains an interferometer, one or more detectors, and other portions of the system. Various examples of the essentially unlimited types of sampling modules are disclosed. Also, automatic sample loading and unloading devices are disclosed, which are feasible because of the modular construction. And means of loading and unloading samples without purge loss are disclosed, which are feasible because of the modular construction.

10 Claims, 14 Drawing Figures

UNIVERSAL SPECTROMETER SYSTEM HAVING MODULAR SAMPLING CHAMBER

BACKGROUND OF THE INVENTION

The present invention relates to Fourier Transform Infrared (FTIR) spectrometry systems. Its essential thrust is a departure from an approximately 40-year tradition, in order to make the systems maximally adaptive to the needs of the user.

The user of a spectrometer wants its functions to be as broad, i.e., universal, as possible. In other words, the user wants flexibility: (a) flexibility in handling different types of samples, e.g. liquids, gases, powders, coated metals; (b) flexibility in illuminating the samples in various ways, e.g., reflection, transmission, multiple internal reflection; and (c) flexibility in types of information obtained.

Two prior applications assigned to the assignee of this application illustrate advanced designs of "accessories" provided for installation as sample-illuminating apparatus in conventional FTIR spectrometer systems.

Application U.S. Ser. No. 580,120, filed Feb. 14, 1984, as a continuation of application U.S. Ser. No. 291,402, filed Aug. 10, 1981, discloses a sample-illuminating accessory for spectroscopic use, in which the radiation leaving the sample holder is traveling in essentially the same direction as the radiation reaching the sample holder. This accessory is applicable both as a transmission-type apparatus in which the radiation passes through the sample, and as a multiple internal reflectance (MIR) apparatus in which the radiation enters at one end of a sample holder providing an enclosed reflecting path and is reflected repeatedly before leaving the sample holder.

Application U.S. Ser. No. 298,067, filed Aug. 31, 1981, now U.S. Pat. No. 4,473,295, issued Sept. 25, 1984, discloses a sample-illuminating accessory for spectroscopic use, in which the radiation leaving the sample holder is traveling in a direction different from the radiation reaching the sample holder because of its reflectance by the sample. The accessory is designed to function either in a diffuse reflectance mode or a specular reflectance mode.

Both of the prior applications identified above provide sample-illuminating accessories carefully designed to fit into a sample chamber located in the spectroscopic instrument.

Applicant has now realized that such systems are unnecessarily constraining, in terms of the options available to the user of the spectroscopic instrument. As stated above, the unnecessary constraints have existed for about 40 years. The apparent reasons for such limitations have been: (a) a tendency of instrument designers to focus primarily on their own requirements, as distinguished from those of the users; and (b) the unchallenged practice of following, in the design of FTIR spectrometer systems, the same paths which had been followed in the design of "dispersive" spectrometer systems, in which wavelength encoding has been accomplished by using a diffraction grating or a prism to spectrally disperse the radiation, which is focused at an entering slit, passes through the sample, and is then diverging as it emerges from the slit. The accessory complications caused by such focusing requirements are discussed in the "Background" portions of the identified prior applications.

Because the list of available functions for FTIR spectroscopy is long and growing, a major purpose of the present invention is to permit the user of spectroscopic systems to accomplish most or all of those spectroscopy functions with a single basic system, and to interchange such functions easily, and without loss of precision. Maximum flexibility is thus provided for the user, who may be a forensic analyst examining microscopic samples, a biological researcher doing in vivo analysis, or a quality control manager needing to process hundreds of samples a day with minimum operator involvement.

Another major purpose of the present invention is to eliminate wasted time. Heretofore, most FTIR spectrometers have made time saving improvements primarily in data acquisition. The present invention recognizes and deals with the remaining time factors, including the time required between insertion of successive samples, and the time required for converting from one sample-illuminating mode to another.

SUMMARY OF THE INVENTION

The present invention provides a modular design, in which the basic spectrometer is contained in a housing having interferometer and detection sub-assemblies, whereas the sample chamber is provided by a separate housing which is readily attachable to, and detachable from, the spectrometer housing. This permits a plurality of separate sample measuring modules to be built, and substituted for one another, very quickly and without risk of mishandling. Each sample compartment is simply bolted to one side of the spectrometer housing. A collimated pre-sample beam from the interferometer sub-assembly enters the bolted-on sample module through aligned apertures in the engaging walls of the two housings and, at a laterally-spaced location, a collimated post-sample beam passes from the sample module to the detector sub-assembly through aligned apertures in the same engaging walls of the two housings.

This arrangement essentially removes limits on the size and shape of the sampling modules, and on the location of the observed samples. It also provides maximum access to each sample module without disturbing the basic spectrometer hardware. In effect, all but one side of the sampling module is readily accessible.

The present invention may use this easy sample chamber accessibility, without entry into the rest of the spectrometer, to provide significant time-saving features. One such feature is an efficient automatic sample loading apparatus. Another such feature is a minimal purge loss mechanism for sample insertion and removal.

DETAILED DESCRIPTION OF SPECIFIC EMBODIMENTS

Figure 1:
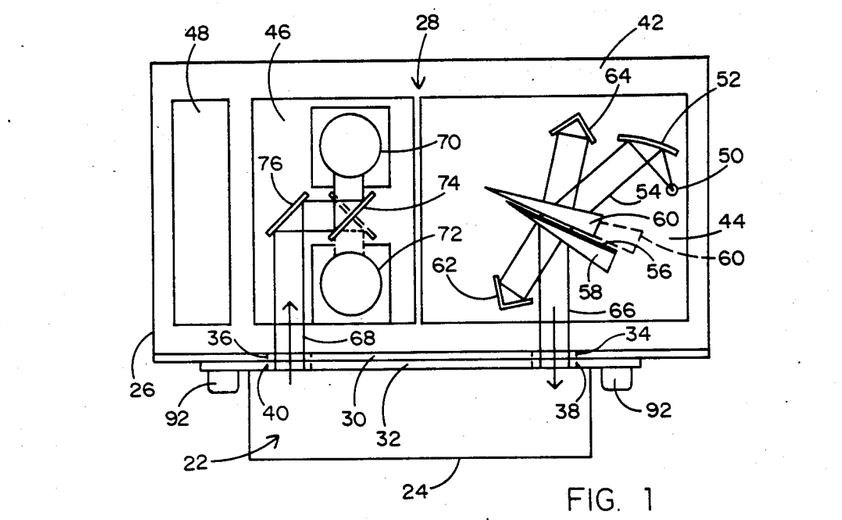
FIG. 1 is a plan view showing the relative locations of the interferometer portion, detector portion, and interchangeable sampling module of applicant's spectrometer.
Figure 2:
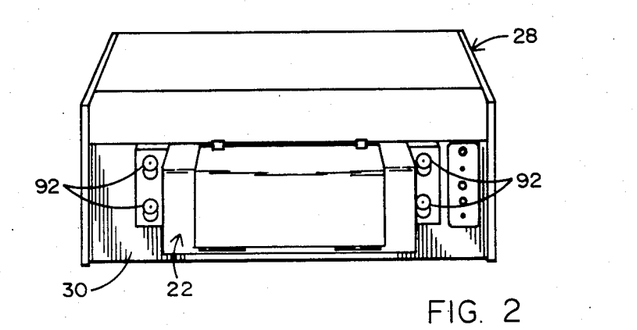
FIG. 2 is an external view of the system shown in FIG. 1.

As shown in FIGS. 1 and 2, an interchangeable sampling module 22 includes pre-arranged and pre-aligned sample-illuminating optics located inside a housing 24, which is separate from, but readily attachable to, and detachable from, a housing 26 containing an interferometer/detector module 28. Both housings 24 and 26 are enclosed during spectrometer operation, except for aligned apertures, through which pass two laterally-spaced collimated radiation beams. One pair of aligned apertures transmits a collimated beam from the interferometer to the sample module, and another pair of aligned apertures transmits a collimated beam from the sample module to the detector.

As seen in FIG. 1, the side of the interferometer/detector module 28 which is engaged by the sampling module 22 has an interface panel 30, to which is clamped the rear wall 32 of whichever sampling module is currently in use. Interface panel 30 has two spaced apertures 34 and 36, which are aligned, respectively, with spaced apertures 38 and 40 in wall 32.

Inside the housing 26 of the interferometer/detector module, separate sub-assemblies may be mounted on supporting plates, which are secured to the floor 42 of housing 26. For example, the interferometer portion may be carried on a plate 44, the detector portion may be carried on a plate 46, and the electronics portion may be carried on a plate 48.

Although the specific interferometer structure may be freely varied within the scope of the present invention, applicant has determined that a particularly practical interferometer for the present invention is the refractive type disclosed and claimed in Doyle U.S. Pat. Nos. 4,190,366; 4,165,938; and 4,265,540;, all assigned to the assignee of the present application. Interferometers of this type are identified in the trade literature as the "Transept (TM)" interferometers. The advantage of the Transept interferometer lies in its rugged reliability. It is essentially immune to mechanical and thermal disturbances and other physical stresses encountered in industrial situations. The smaller sampling modules are "hung on" the interface panel 30 (i.e., they need not be mechanically self-supporting). The sturdy characteristics of the Transept interferometer are thus particularly useful in conjunction with the present invention in that they allow the instrument to operate reliably even when subjected to the varied stresses resulting from hanging diverse modules on the instrument.

The interferometer in FIG. 1 includes a radiation source 50 and optics 52 which direct a collimated beam 54 toward a beamsplitter coating 56 located on the inner surface of a non-moving wedge-shaped prism 58. A moving wedge-shaped prism 60, which has the same dimensions as prism 58, causes spectral scanning of the interferometer. The beam-splitter 56 transmits part of the source radiation along one interferometer arm toward a first stationary corner reflector 62, and reflects part of the source radiation along the other interferometer arm toward a second stationary corner reflector 64. The returning collimated beams from the respective reflectors 62 and 64 are recombined at beamsplitter 56; and a recombined collimated beam 66 exits the interferometer and enters the sampling module through aligned apertures 34 and 38.

After sample illumination in the sampling module, a collimated beam 68 exits the sampling module and enters the detector portion of the system through aligned apertures 40 and 36. The detectors convert the optical signals into electronic signals for suitable electronic processing. In FIG. 1, two detectors 70 and 72 are shown, which may provide alternative types of detection. Selection of the detector is controlled by moving a "detector-switching" flat mirror 74 either to a position in which radiation is directed to detector 72 or to a position in which radiation is directed to detector 74. Another flat mirror 76 may be needed to direct beam 68 toward mirror 74. One detector may be a general purpose, broad band detector, and the other may be a mercury-cadmium-telluride cooled detector optimized for high sensitivity.

The collimated beams 66 and 68 which enter and leave the sampling module 22 are preferably, although not necessarily, parallel to one another. Parallelism of the beams tends to simplify the optical arrangements within the various interchangeable sampling modules.

An "open geometry" approach is provided by the sample region which is exterior to, and detachable from, the main body of the spectrometer. This permits an unlimited number of sampling modules to be pre-arranged and permanently configured for different analytical procedures. The optical elements in each sampling module are pre-located, pre-aligned, and generally optimized for a given operation. This permits substantial pre-configuration at the manufacturing source. And it also permits pre-configuration of experimental set-ups by optical technicians, with no further action required by the experimenter, except unbolting one sampling module from the main body and then bolting on the next sampling module. Because the in and out beams are collimated, no alignment problems are encountered by the experimenter.

With collimated radiation, lateral displacement of the sampling module will have no effect on the imaging of the radiation on the detector, unless such displacement is excessive. However, if the radiation were either diverging or converging as it passes between the spectrometer body and the sampling module, any lateral displacement of the module would upset the imaging characteristics of the system. In other words, the radiation would not focus properly on the detector.

Figure 3:
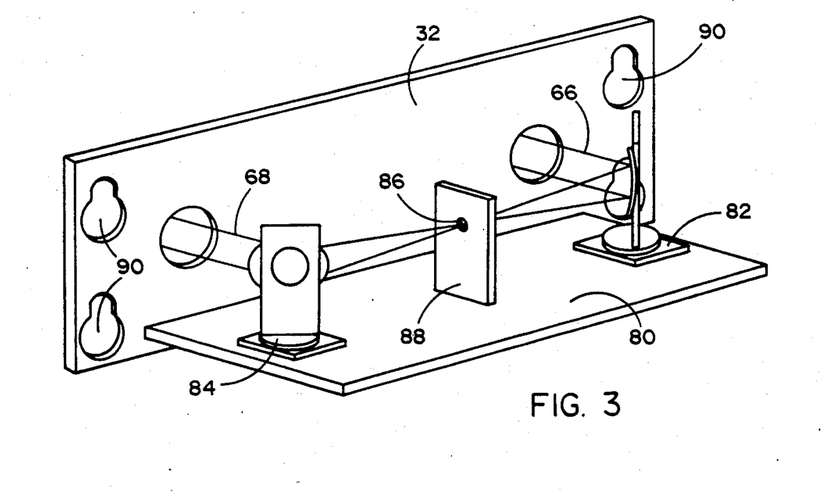
FIG. 3 is an isometric view of a general purpose sampling module platform having focused beams directed toward the center of the sample chamber.

Several figures illustrate various prealigned sampling modules which have already been developed. FIG. 3 shows a standard sampling module configuration having two paraboloid reflectors each opposite one of the collimated beams 66 and 68, which reflectors have a common focal point at a sample-holder location midway between the paraboloids. This configuration is readily adaptable for various experiments involving transmittance of focused radiation through the sample.

Figure 4:
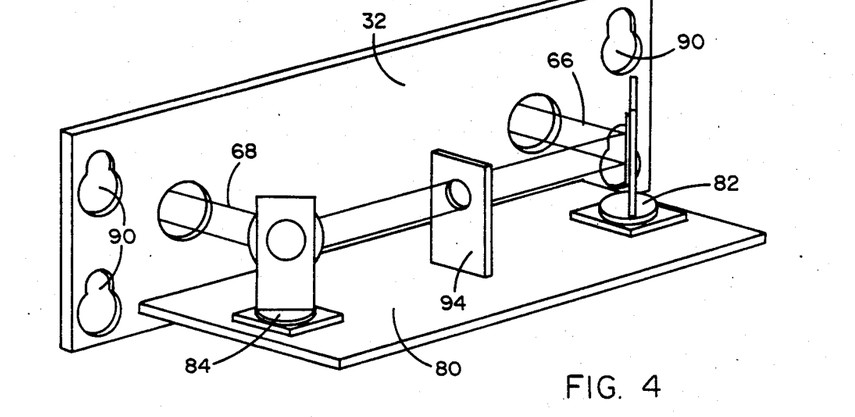
FIG. 4 is an isometric view of a general purpose sampling module platform having collimated beams directed toward the center of the sample chamber.

FIG. 4 shows a standard sampling module configuration having two flat mirrors, instead of two paraboloids, each opposite one of the collimated beams 66 and 68, which flat mirrors reflect collimated radiation toward the center of the sample chamber. This configuration is readily adaptable for various experiments involving IR accessories, such as those which use sample-adjacent paraboloids for sample-reflectance measurements (diffuse or specular).

Figure 5:
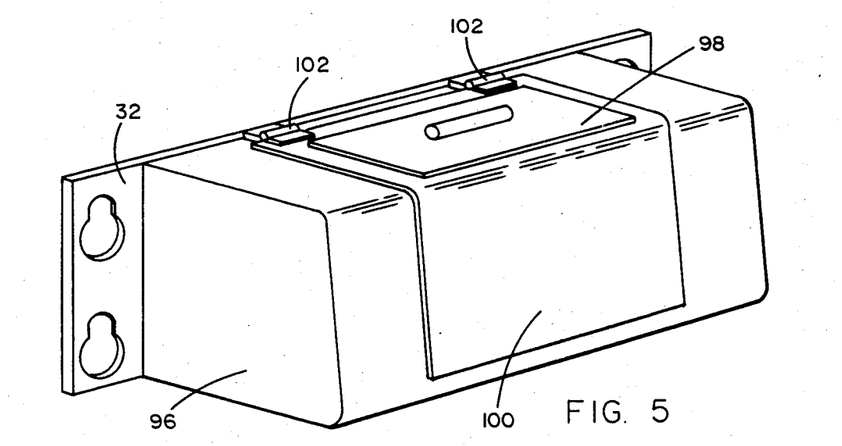
FIG. 5 is a covering structure suitable for the sampling modules of both FIGS. 3 and 4.

FIG. 5 shows a covering structure applicable to the optical combinations of both FIGS. 3 and 4.

As shown in FIG. 3, the wall 32 of the sampling module is adapted to engage the interface panel 30 of the main body of the spectrometer. Wall 32 carries a platform 80, which in turn carries two position-adjustable mirror supports 82 and 84 located opposite the respective collimated beams 66 and 68. Each mirror support 82 and 84 carries a paraboloid reflector having its focal point at the location 86 of a sample carried by a sample holder 88. This sample chamber configuration provides a sample region beam geometry similar to that encountered in many commercial spectrometers. Wall 32 has four "keyhole" apertures 90, the larger lower portions of which pass over the heads of thumbscrews 92 (see FIGS. 1 and 2) used to secure wall 32 tightly against interface panel 30 of the main body. The bodies of the screws fit through the smaller upper portions of the apertures 90; and the screw heads are tightened against wall 32.

As shown in FIG. 4, the two adjustable mirror supports 82 and 84 (mounted on platform 80) each carry a flat mirror mounted at a 45° angle to the respective beam 66 or 68, instead of a paraboloid reflector (as in FIG. 3). This structure retains the collimated shape of the beam at the location of a vertical support member 94, which provides a reference position for whatever sample holder, or optical structure, may be inserted in the sample chamber. For example, a pair of paraboloids which focus at a common point on a reflecting sample may be inserted, similar to those disclosed in U.S. Pat. No. 4,473,295.

FIG. 5 shows a suitable cover for the sample chamber of either FIG. 3 or FIG. 4. An enclosure, or shroud, 96 is secured to the wall 32. Preferably two access covers are used. A small access cover 98 permits opening the chamber for sample removal or insertion with minimum perturbation of the gas which fills the closed chamber. A large L-shaped access cover 100 is positioned by hinges 102. Lifting cover 100 provides greater access for working with the optical elements inside the sample chamber.

From the above description, it is apparent that the sample chamber is a modular unit external to the main body of the spectrometer, but nevertheless readily attachable to, and detachable from, the main body, with very slight loss of time. The sample chamber optics should be pre-configured and pre-aligned by a skilled technician, thus freeing the experimeter, e.g., the chemist, to concentrate on running experiments as efficiently as possible.

The external location of the sampling module provides maximum accessibility to its interior, without entering the main body of the spectrometer. Five sides of the sampling module—top and bottom, front, and both ends—are directly accessible for such purposes as (a) automatic loading and unloading, and (b) changing samples with a minimum of "purge" loss in the system. All of the cited advantages reduce overall operating time, and radically increase the productivity potential of the spectrometer.

The reference to improved purge retention, which will be illustrated in detail below, pertains to the fact that most spectrometer analyses should be performed in a special gas environment, such as dry nitrogen. If the experiments were performed in normal atmospheric conditions, undesired optical artifacts would be introduced, primarily by water vapor and by carbon dioxide.

In order to avoid these sources of inaccuracy the entire spectrometer should be enclosed, and maintained in a "purged" atmosphere. The purging is accomplished by admitting dry nitrogen at one point, and permitting the normal atmosphere to escape at any closed but unsealed locations. Normally purging is accomplished by connecting a hose from the rear of the main body to a source of nitrogen, which may be a suitably valved tank of liquid nitrogen. The purging gas is retained in communication with the spectrometer throughout the series of analytical procedures. After initial purging has been completed, the experiments may be started. Since initial purging is a time-consuming process, it is highly desirable to avoid intrusion of atmosphere, i.e., loss of purge, during the interchanging of samples. The present invention permits the attainment of substantially zero purge loss during sample interchange.

Figure 6:
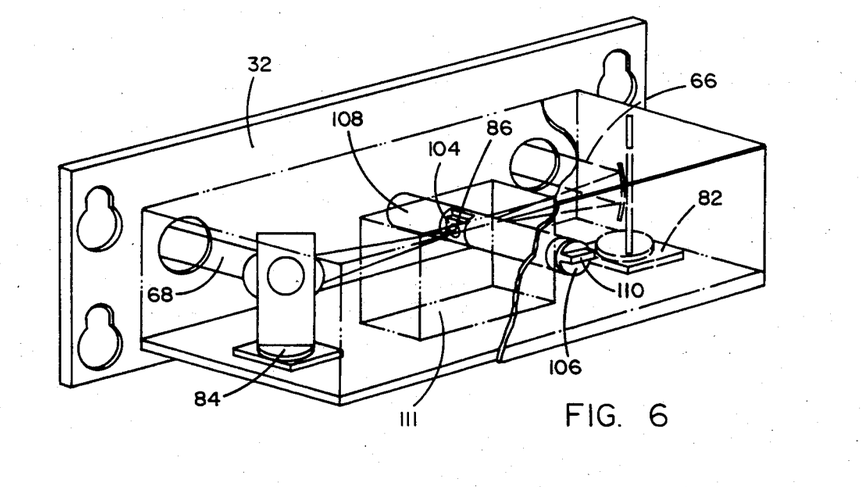
FIG. 6 is an isometric view of a sampling module, similar optically to FIG. 3, but incorporating a minimal purge loss feature.

FIG. 6 shows the incorporation of a minimal purge loss structure in a sampling module similar to that shown in FIG. 3. As in FIG. 3, the mirror supports 82 and 84 carry paraboloid reflectors having their common focal point at the sample. The sample 86, which may be solid or liquid, is mounted in a small metal block 104. The block is retained in position in a recess intermediate the ends of a plunger 106. This plunger, which is preferably cylindrical, has a close, sliding fit inside an elongated cylindrical tube 108, the fit being tight enough to substantially prevent air leakage into the sample chamber. Tube 108, in turn, extends through an aperture in the front wall of the sample chamber, and is secured in place in a supporting frame 111. The cylindrical body of the plunger 106 extends into tube 108 beyond the location of sample block 104. Thus one sample can be removed and another substituted without opening the chamber interior, because the inner end of the plunger still blocks the wall aperture during sample interchange. When the plunger holding the new sample is pushed back into the tube to locate the sample at the focal point of the beams, the only air brought into the chamber is that in the space around the small metal block 104. No delay is required for purging this amount of air. A flat projection, or knob, 110 on the outer end of plunger 106 permits rotation of the plunger to adjust the sample position inside the chamber.

The "zero" purge loss structure, which has just been generally described, will be the subject of a separate, much more detailed, application, which will have the same assignee as the present application.

Figure 7:
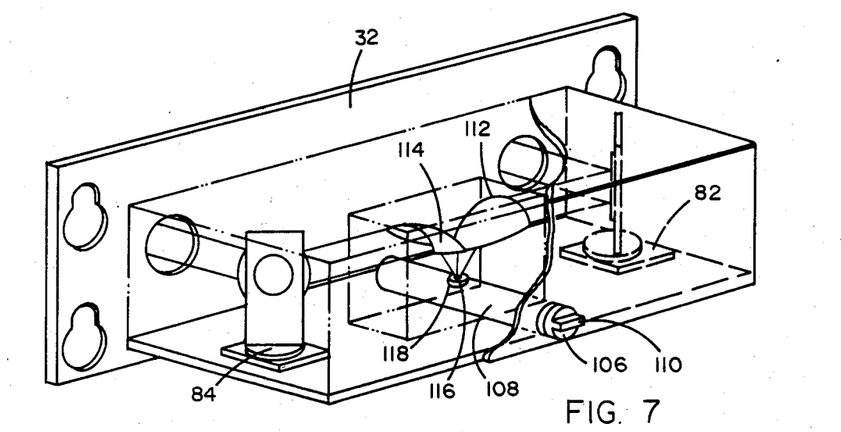
FIG. 7 is an isometric view of a sampling module, which uses collimated radiation as does FIG. 4, but which also incorporates a minimal purge loss feature.

FIG. 7 shows the use of the purge retention structure in a sampling module similar to that of FIG. 4, which also incorporates optical elements used for reflectance analysis of a sample surface. The two flat mirrors carried, respectively, by mirror supports 82 and 84, provide collimated colinear beams. Two paraboloid reflectors 112 and 114 have coinciding focal points at the surface of a sample 116, which may be a powder causing diffuse reflectance, or a surface causing specular reflectance. Assuming that the sample is a powder, its holder must face upwardly, as shown. As in the sampling module of FIG. 6, a plunger 106, having a knob 110, extends into a cylindrical tube 108. A small sample holder 118 is carried by plunger 106, and is brought into the sample-illuminating position by suitable adjustment of the plunger's position. As in the structure of FIG. 6, removal of one sample, and substitution of another, requires minimal air entry into the chamber, thus eliminating time loss for purging.

In the sampling modules of both FIGS. 6 and 7, the direct access to the sample chamber from its front surface is important in providing a relatively short distance through which the plunger 106 is required to extend. Vertical access would be possible in the module of FIG. 6, but not in the module of FIG. 7, where a powder sample must be held in place.

Figure 8:
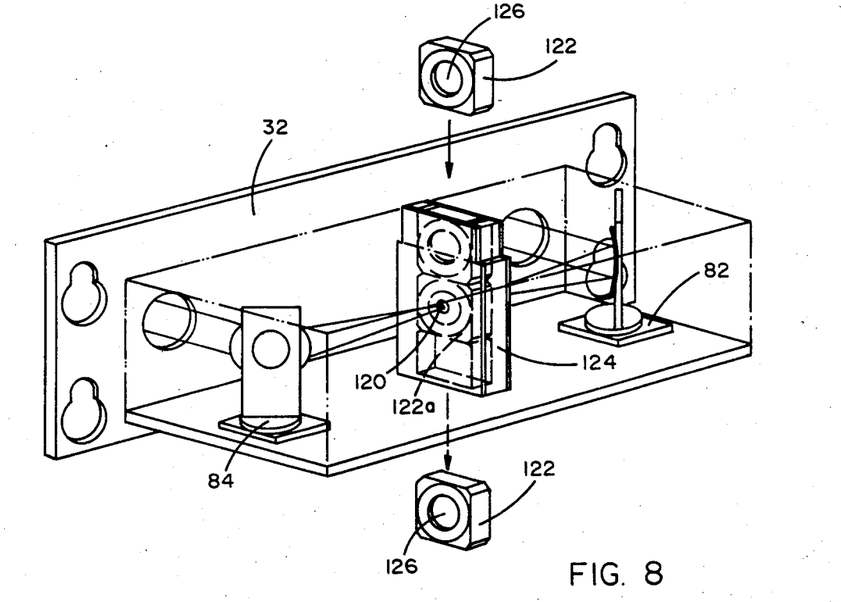
FIG. 8 is an isometric view showing a sampling module designed to permit rapid "pass-through" loading and unloading without purge loss.

FIG. 8 shows a sampling module designed to permit automated sample loading and unloading without purge loss. In this module, which is designed for transmittance of radiation through the samples, the adjustable mirror supports 82 and 84 carry paraboloid reflectors, whose common focal point is at the sample position 120. In order to permit particularly rapid insertion and removal of samples, which may be part of an automated process, the sample holders are inserted at the top of the chamber, moved to, and held at, the focal point during analysis, and then removed by "dropping out" at the bottom of the chamber. A plurality of sample holders 122 are shown in FIG. 8, each of which is a small metal block. Each metal block is shaped to fit in, and slide vertically downward through, a vertical channel-forming element 124. Each sample holder has a centrally-located sample 126, through which the focused radiation passes when its holder is in the position shown at 122a. The samples may be solids or liquid cells. Because the metal blocks which act as sample holders are designed to fill the cross-sectional area in the vertical channel-forming element 124, the insertion and removal of samples is accomplished without purge loss.

Figure 9:
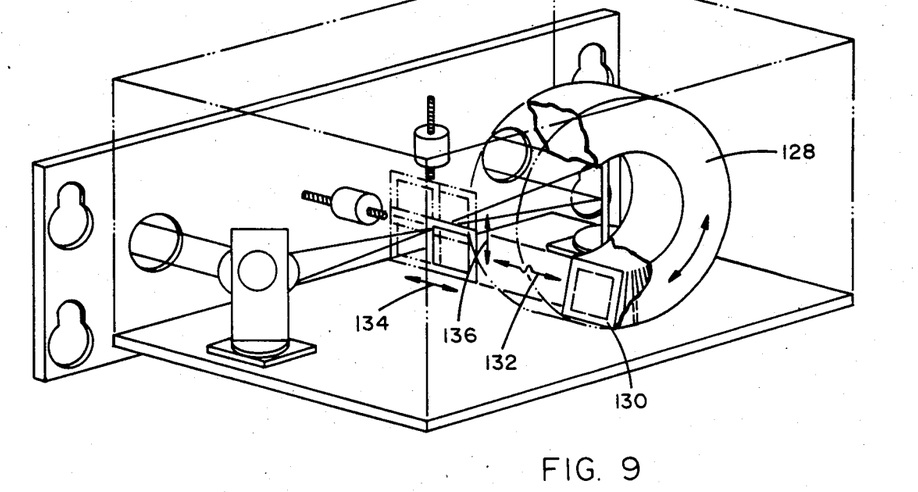
FIG. 9 is an isometric view showing a relatively complex sample-loading and sample-handling structure located inside a sampling module.

FIG. 9 shows a much more complex automated arrangement. Within the sample chamber are both (a) a carousel 128 which carries a large number of sample holders 130, and (b) means for handling each sample holder in turn, capable of moving it along the paths indicated by the arrows 132, 134 and 136 in the figure.

Further details of the automatic sample handling systems of FIGS. 8 and 9 will be described in separate, but related, patent applications.

Figure 10A:
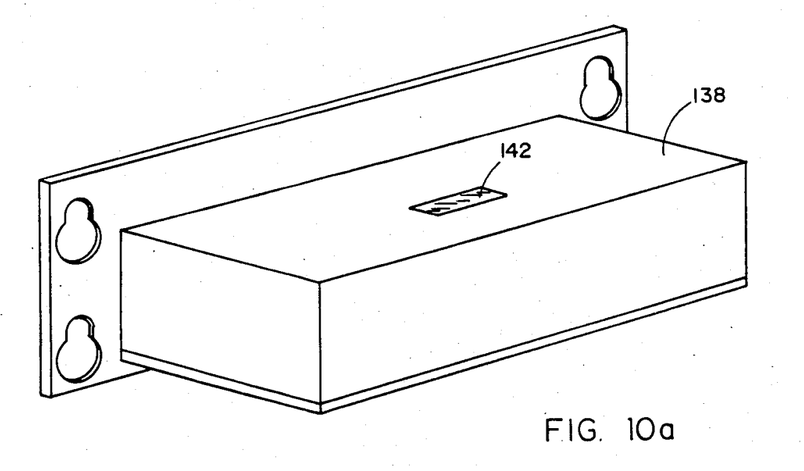
FIGS. 10A, 10B and 10C are views illustrating a sampling module incorporating an ATR (attenuated total reflectance) crystal.
Figure 10B:
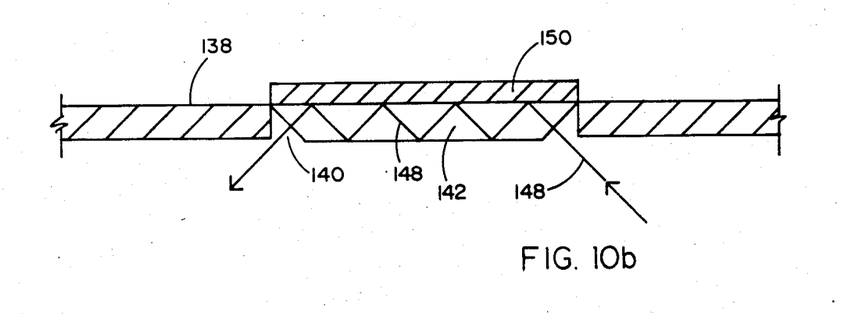
Figure 10C:
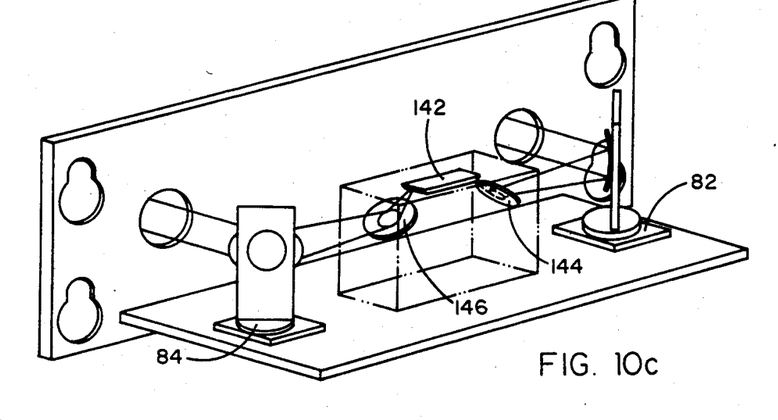

FIGS. 10A, 10B and 10C disclose a very different use of the sampling module. As in the previous figures, the sampling module is contained within a fully enclosed housing (see FIG. 10A). As seen best in the sectional view of FIG. 10B, the upper surface 138 of the housing cover has a centrally located aperture 140 which is filled by an ATR (attenuated total reflection) crystal 142, the material of which may be KRS-5, zinc selenide or germanium. In FIG. 10C, the general radiation path in the sample chamber is shown diagrammatically. The mirror supports 82 and 84 carry paraboloid reflectors. Their reflected beams are again reflected by flat mirrors 144 and 146, which cause them to focus at opposite ends of crystal 142. The rays pass through the crystal in the manner indicated by line 148 in FIG. 10B, entering at the right end as shown by the arrow, reflecting back and forth between the upper and lower surfaces of crystal 142, and exiting at the left end as shown by the arrow. A sample 150 is laid on top of crystal 142, and the reflections from the sample provide the desired data. Here again, sample changing entails no purge loss. The easy accessibility of the sample to the optical system is made possible by the use of the separate sampling module.

Figure 11:
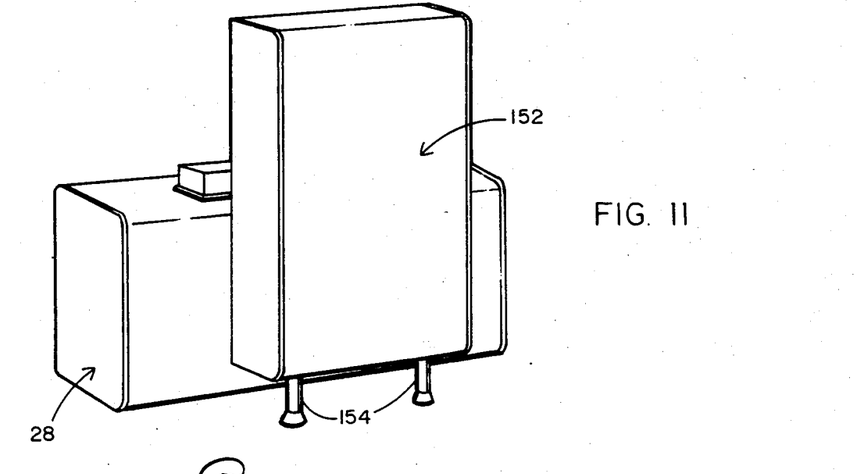
FIG. 11 is an external view of a system incorporating a microscope sampling module which requires standalone support and houses its own detector.

FIG. 11 shows the exterior of a module chamber 152 which is much too large and heavy to be supported by the front wall of the spectrometer body 28. The module 152 differs from those in other embodiments both in providing its own supporting legs 154, and in having its own internally-contained detector.

Figure 12:
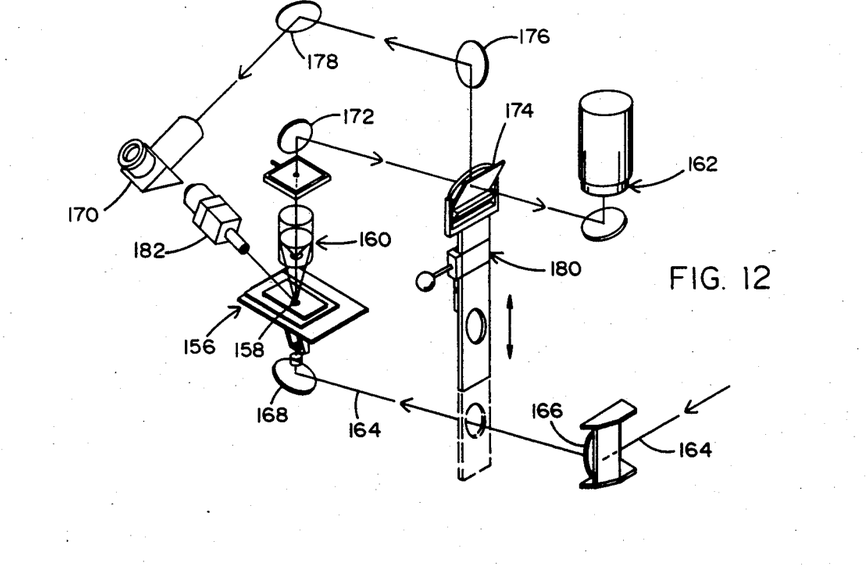
FIG. 12 is a schematic diagram showing the internal elements of the sampling module of FIG. 11.

The sampling module 152 is a microscope module, whose internal system is shown diagrammatically in FIG. 12. It provides the ability to examine sub-nanogram samples rapidly, efficiently, and easily, with little or no sample preparation. Its primary components, as seen in FIG. 12, are a horizontal/vertical stage 156 on which a sample 158 is supported, a condenser lens 160 focusing radiation on the sample, and a detector 162 (preferably HgCdTe). An infrared beam is shown entering at 164, and being reflected toward the sample by mirrors 166 and 168.

The sample may be viewed either by the operator through an eyepiece 170, to which light is directed by mirrors 172, 174, 176 and 178, or by detector 162. A manually controlled beam stop 180, which carries mirror 174, in its solid line upper position provides for operator viewing. In its lower, dashed line position, it permits the IR radiation from the sample to reach detector 162 for analysis. A stage illuminator 182 provides light for the operator's use in adjusting the position of the sample, by manipulating the stage 156.

The possibility of combining the microscope module 152 with the basic spectrometer unit 28 illustrates the essentially unlimited ability of the modular sample chamber system to extend the functions of the spectrometer unit, and to enhance its value to the user.

The modular system provides an optimized instrument for almost any purpose, including: (1) a dedicated pharmaceutical analyzer for screening hundreds of powdered drug samples per day; (2) an automated system for running an extensive series of liquid samples with no operator involvement other than sample preparation; and (3) stand-alone, full performance microspectrometer, capable, for example, of analyzing the individual grains of the various components in a crushed APC tablet.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A spectrometer system comprising:
    an interferometer sub-assembly from which a first collimated beam is output;
    a detector sub-assembly toward which a second collimated beam is input;
    the first and second collimated beams being parallel to one another;

means for enclosing the interferometer sub-assembly and the detector sub-assembly, said means providing first and second apertures for the first and second collimated beams, respectively;

a unitary accessory enclosure adapted to be readily attached to, and readily detached from, the enclosing means, said enclosure having apertures aligned with said first and second apertures;

a first mirror which is supported inside the accessory enclosure, and which is arranged to reflect the entire first aperture radiation beam at a ninety degree angle;

a second mirror which is supported inside the accessory enclosure, and which is arranged to reflect the entire second aperture radiation beam at a ninety degree angle; and means for purging both the sub-assembly enclosing means and the accessory enclosure so as to replace the normal atmosphere with an optically non-interfering gas.

2. The spectrometer system of claim 1 wherein the sample containing module comprises:
a rear-wall-forming plate having integral portions which extend beyond the end walls of the module; and
means for holding the extending portions of the plate against the enclosing means.

3. The spectrometer system of claim 1 in which the first and second mirrors are confocal paraboloids.

4. The spectrometer system of claim 1 in which the first and second mirrors are flat reflectors which provide co-linear collimated beams between them.

5. The spectrometer system of claim 4 which also includes:
a pair of confocal paraboloids located between the first and second flat reflectors, and having their common focal point laterally spaced from the co-linear collimated beams.

6. In a spectrometer system having an interferometer sub-assembly, a detector sub-assembly, and means for enclosing the interferometer sub-assembly and the detector sub-assembly, said enclosing means having first and second apertures:
means for causing an interferometer-modulated collimated analytical beam from the interferometer sub-assembly to exit the enclosing means through the first aperture;
means for passing to the detector sub-assembly a collimated radiation beam which enters the enclosing means through the second aperture;
a readily-detachable sample-containing module attached to the enclosing means, and having two apertures aligned with the first and second apertures, respectively;
means in the module for receiving the collimated radiation which exits from the first aperture, for illuminating the sample, and for directing post-sample collimated radiation through the second aperture;
a hollow guiding member extending from the exterior of the sample-containing module into the interior thereof beyond the point where sample illumination occurs; and
sample-carrying means insertable in the hollow guiding member in such a way as to block ingress of atmosphere to the interior of the module;
each sample being removable from the interior of the module without permitting ingress of atmosphere to the interior of the module.

7. The spectrometer system of claim 6 wherein each sample is caused to move into the hollow guiding member at one wall of the module, is illuminated inside the module, and is then caused to eject from the module at the opposite wall thereof.

8. The spectrometer system of claim 6 wherein the sample-carrying means is a plunger-like member having a sample receptacle intermediate its ends, thereby permitting each sample, after illumination, to be removed through the same module wall aperture through which it entered without permitting ingress of atmosphere to the interior of the module.

9. The spectrometer system of claim 7 wherein the entering wall of the module through which each sample enters is the top wall, and the exiting wall of the sample module through which each sample exits is the bottom wall.

10. The spectrometer system of claim 8 wherein the wall of the module through which each sample is inserted and removed is the front wall, i.e., the wall opposite the enclosing means to which the module is secured.

* * * * *